(12) United States Patent
Uhrlandt et al.

(10) Patent No.: US 6,613,309 B2
(45) Date of Patent: Sep. 2, 2003

(54) INHOMOGENEOUS SILICAS IN DENTAL CARE COMPOSITIONS

(75) Inventors: Stefan Uhrlandt, Niederkassel (DE); Ralf Schmoll, Bonn (DE); Arnold Storeck, Frankfurt am Main (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/098,595

(22) Filed: Mar. 18, 2002

(65) Prior Publication Data

US 2003/0068281 A1 Apr. 10, 2003

(30) Foreign Application Priority Data

Mar. 16, 2001 (DE) .......................... 101 12 650

(51) Int. Cl.⁷ ............................. A61K 7/16; C01B 33/12
(52) U.S. Cl. ..................... 424/49; 423/335; 423/339
(58) Field of Search ............... 424/49–58; 423/335, 423/339

(56) References Cited

U.S. PATENT DOCUMENTS

| | | | | |
|---|---|---|---|---|
| 3,538,230 A | * | 11/1970 | Pader et al. | |
| 3,689,637 A | * | 9/1972 | Pader | |
| 3,705,940 A | * | 12/1972 | Kirchgassner | |
| 4,132,806 A | * | 1/1979 | Wason | |
| 4,485,089 A | * | 11/1984 | Leipold | 424/49 |
| 4,704,270 A | * | 11/1987 | Muller et al. | |
| 4,731,194 A | * | 3/1988 | Rossmann et al. | 252/168 |

FOREIGN PATENT DOCUMENTS

| | | | |
|---|---|---|---|
| GB | 1241877 | * | 8/1971 |
| GB | 1298130 | * | 11/1972 |
| GB | 1400793 | * | 7/1975 |
| GB | 1433743 | * | 4/1976 |

* cited by examiner

*Primary Examiner*—Shep K. Rose
(74) *Attorney, Agent, or Firm*—Oblon, Spivak, McClelland, Maier & Neustadt, P.C.

(57) ABSTRACT

A silica comprising at least two silica fractions, wherein the at least two silica fractions differ by at least 10% in at least one of their BET surface area values, their CTAB surface area values or their DBP absorption values, the ranges of these three physicochemical properties being as follows:

| | |
|---|---|
| BET surface area | 30–300 m²/g |
| CTAB surface area | 30–300 m²/g |
| DBP absorption | 80–300 g/100 g. |

21 Claims, No Drawings

INHOMOGENEOUS SILICAS IN DENTAL CARE COMPOSITIONS

BACKGROUND OF THE INVENTION

1. Field of the Invention

The present invention relates to silicas having an inhomogeneous structure or composition, to processes for preparing them, and to their use in dental care compositions.

2. Description of the Background

Readily dispersible silicas are prepared, for example, in accordance with EP 0 901 986 or EP 0 647 591 by precipitating waterglass with sulfuric acid, followed by drying. The dried products are subsequently ground and/or granulated.

In another process, silicas are prepared, likewise by acid precipitation, but are dried by being sprayed in hot air and at the same time shaped into beads, which are easily destroyed. Thus EP 0 18 866 describes the preparation of spray-dried silica having an average particle diameter of more than 80 $\mu$m, the particles being solid and possessing a homogeneous structure.

For use in dental care compositions, important parameters for silicas include not only their thickening action and abrasiveness, but also their specific surface areas (BET, CTAB) and their oil absorption capacity (DBP).

Since only specialty silicas, i.e., silicas that are complicated to prepare, combine sufficient thickening action and abrasiveness, dental care compositions normally utilize two different types of silica.

A need therefore continues to exist for a method of preparing a silica which at one and the same time covers broad ranges of physicochemical data such as BET or CTAB surface area, and has good abrasiveness in conjunction with a good thickening action.

SUMMARY OF THE INVENTION

Accordingly, one object of the present invention is to provide a silica material which is not only characterized by broad ranges of physicochemical data such as BET or CTAB surface area, but also has good abrasiveness in conjunction with a good thickening action.

Briefly, this object and other objects of the present invention as hereinafter will become more readily apparent can be attained by a silica material comprising at least two silica fractions, wherein the at least two silica fractions differ by at least 10% in at least one of their BET surface area values, their CTAB surface area values or their DBP absorption values.

DETAILED DESCRIPTION OF THE PREFERRED EMBODIMENTS

It has surprisingly been found that silica that has an inhomogeneous composition is readily adjustable to meet the requirements needed for silicas used in dental care compositions. Moreover, the silica of the invention produces little dust when handled, thereby facilitating handling of the material and prevents dust contamination of customer's plants.

The silicas of the invention are particularly suitable as fillers in dental care compositions. The abrasive figures of the silicas of the invention according to the RDA method are within the range of 45% to 70% that is typical for modern toothpaste silicas, but may also lie above or below this range, depending on the chosen mixture of the precipitating suspensions and on their technical preparation. Likewise within the typical flow range are the toothpastes prepared from these silicas. In the shear stress tests, in fact, they have a shear rate of from 100 s$^{-1}$ to 500 s$^{-1}$ up to a shear stress of 600 Pa, depending on the silica mixture of the invention that is used and on the concentration that is used in the paste. Higher or lower shear rates within the specified shear stress range may occur depending on the chosen mixture of the precipitating suspensions and on their technical preparation.

The structure of the silica material of the invention, comprising at least two silica fractions, results in an inhomogeneity of the product silica, which is reflected at the same time in good abrasiveness and thickening action and also in a low fines content.

Silicas of the invention possess a fines content of not more than 10% with a particle diameter of less than or equal to 63 $\mu$m (Alpine sieve residue).

A similar concept, i.e. inhomogeneous silicas, is disclosed in EP 0 942 029. In this publication rubber compositions are described which comprise a precipitated silica in two different aggregate sizes. The different aggregate sizes are employed for the ready dispersibility of the silica in the rubber blend.

The different silica fractions of the present invention are not described in the publication. Moreover, in the present case a different aggregate size of the silica fractions is of secondary importance. What is important, however, is that the silica fractions differ in their physicochemical data.

For the purpose of the present invention, silica fractions refer to different grades of silicas which result from different processes of preparation or process variants, and thereby have a difference of 10% in their values of at least one of the above-mentioned physicochemical properties. Such a difference exists preferably for two, with particular preference three, of these parameters.

The differences in the abovementioned parameters may be obtained by means of different processes of preparing the silica fractions. Accordingly, all, one or more of the silica fractions may be precipitated silicas and/or pyrogenic silicas. In the case of precipitated silicas, in particular, it is possible to obtain different silica fractions by means of different precipitation processes. Silicas of the invention may also be prepared from fractions of precipitated and pyrogenic silicas.

For precipitated silicas, a variety of precipitation methods are known and are described, for example, in EP 0 901 986, EP 0 937 755, EP 0 643 015 and EP 0 647 591. In the publications, illustratively, two precipitated silicas from different preparation processes can be processed to give the inhomogeneous silica of the invention.

The silica fractions may be precipitated silicas or pyrogenic silicas, and the fractions may be mixed at different steps in the process that are normally carried out in the preparation of silicas.

When using fractions of precipitated silicas, mixing may take place following the precipitation of silicate with an acid (generally waterglass, i.e., sodium silicate, with sulfuric acid) by mixing together the precipitation suspensions or the filtercakes obtained following filtration of the suspensions, and also liquefied (resuspended) filtercakes. It is also possible to add ready-prepared and dried silica fractions, as solids, to the suspensions or to the filtercakes.

The mixtures obtained in this manner may have to be filtered and dried by a customary technique. Examples of drying processes are spray drying, nozzle spray drier, rack drier, rotary tube drier, and spin flash drier processes.

Drying may be followed by a final grinding and/or granulation step.

It is also possible to mix the silica fractions in the dry state. This may be followed by resuspension, with the above drying steps, and/or by grinding/granulation.

The silica of the invention may have the following physicochemical data:

| | |
|---|---|
| BET surface area | 30–300 m$^2$/g, especially 30–200 m$^2$/g |
| CTAB surface area | 30–300 m$^2$/g, especially 30–200 m$^2$/g |
| DBP absorption | 80–300 g/100 g |

The above physicochemical data ranges pertain to the silica of the invention per se, and not to the silica fractions which make-up the silica.

In the manner described, the physicochemical data of the silica fractions must differ by at least 10%, preferably by at least 15%, with particular preference by at least 20%.

The physicochemical data are determined by the following methods:

| | |
|---|---|
| BET surface area | Areameter, from Strohlein, to ISO 5794/Annex D |
| CTAB surface area | at pH 9 by the method of Jay, Janzen and Kraus in Rubber Chemistry and Technology 44 (1971) 1287 |
| DBP number | ASTM D 2414-88 |

The present invention also provides a process for preparing silicas comprising at least two silica fractions, in which at least two silica fractions which differ by at least 10% in the values of at one least one property of the properties of the BET surface area, the CTAB surface area and the DBP absorption. The silicas having these different values are mixed with one another.

The proportion of the respective fractions in the suspension or of the silica should in each case range from 5 to 95% by weight, based on the dry silica.

The silica product is preferably obtained, by spray drying, for example, in a particle form having an average diameter of more than 80 μm, in particular more than 100 μm, with particular preference more than 200 μm. The suspension may be spray-dried in the same manner as described, for instance, in U.S. Pat. No. 4,097,771.

The silicas of the invention may be used in dental care compositions such as toothpastes or as an abrasive.

Moreover, the silicas of the invention may be used in all areas of application in which silicas are customarily used, such as in battery separators, antiblocking agents, flatting agents in paints, paper coating slips or defoamers, for example.

The Alpine sieve residue is determined as follows, using in each case a sieve having the stated mesh size (63 μm, 250 μm).

Procedure for Determining the Alpine Sieve Residue:

In order to determine the sieve residue, the silica or silicate sample is passed through a 500 μm sieve in order to destroy any devolatilization agglomerates that may be present. Then 10 g of the sieved sample are placed on the air jet sieve, having a 63 μm sieve mesh, and are sieved at 200 mm water column underpressure. Particles of silica or silicate which settle on the sieve cover of the apparatus are removed by careful tapping on the button of the sieve cover. The sieving operation generally lasts 5 minutes. It is at an end when the residue remains constant, generally evident from a free-flowing appearance. Sieving is then continued for one more minute in order to ensure complete sieving action.

If any agglomerates form, the sieving operation is briefly interrupted and the agglomerates are broken down under gentle pressure using a brush. After sieving, the sieve residue is carefully removed from the airjet sieve and reweighed. The sieve residue is expressed in percent, always in conjunction with the mesh size of the sieve.

Calculation:

$$\% \text{ sieve residue} = \frac{F \cdot 100}{I}$$

F=final weight in grams
I=initial weight in grams
Apparatus
Alpine air jet sieve, laboratory type S 200
Vacuum cleaner or fan
Airjet sieve with sieve mesh 63 μm to DIN 4188
Precision balance Having generally described this invention, a further understanding can be obtained by reference to certain specific examples which are provided herein for purposes of illustration only and are not intended to be limiting unless otherwise specified.

Two silica fractions were prepared, A in accordance with the procedure of U.S. Pat. No. 1,043,282 or DE 24 47 013 and B in accordance with DE 44 23 493, and the suspensions obtained from the precipitations were reacted further in the manner described below.

EXAMPLES

Example 1

The precipitation suspensions of the silica fractions A and B were mixed in a 50:50 ratio. This was done by mixing 80 kg of the precipitated silica A (solids content approximately 170 g/l) with 80 kg of the precipitated silica B (solids content approximately 63 g/l) in a stirred vessel. The resulting mixture was filtered and the filtercake was liquefied with a small amount of acid and sprayed in a nozzle spray drier. The analytical data are compiled in the Table below.

Example 2

The precipitation suspensions of the precipitated silicas A and B were mixed in a 70:30 ratio. This was done by mixing 196 kg of the precipitated silica A (solids content approximately 174 g/l) with 84 kg of the precipitated silica B (solids content approximately 63 g/l) in a stirred vessel. The resulting mixture was filtered and the filtercake was liquefied with a small amount of acid and sprayed in a nozzle spray drier. The analytical data are compiled in the Table below.

Example 3

The precipitation suspensions of the precipitated silicas A and B were mixed in a 30:70 ratio. This was done by mixing 71 kg of the precipitated silica A (solids content approximately 174 g/l) with 142 kg of the precipitated silica B (solids content approximately 63 g/l) in a stirred vessel. The resulting mixture was filtered and the filtercake was liquefied with a small amount of acid and sprayed in a nozzle spray drier. The analytical data are compiled in the Table below.

Example 4

A mixture of the dried silica fractions (50:50) was prepared.

Comparison of the analytical data from Examples 1–4 and of silica fractions A and B:

|  |  | Silica fraction A | Silica fraction B | Differences of fractions A:B in % | Example 1 | Example 2 | Example 3 | Example 4 |
|---|---|---|---|---|---|---|---|---|
| Loss of ignition, DIN | % | 5.0 | 3.0 | 40 | 3.7/7.4 | 2.7/7.0 | 3.4/8.0 | 3.9/7.3 |
| Water content | % | 5.0 | 5.0 | 0 | 3.9 | 4.5 | 4.7 | 3.6 |
| pH reading |  | 6.5 | 6.9 | 5.7 | 6.2 | 6.1 | 6.3 | 6.7 |
| Conductivity | $\mu S$ | 800 | 380 | 52.5 | 440 | 290 | 300 | 480 |
| BET surface area | $m^2/g$ | 195 | 45 | 76.9 | 113 | 89 | 146 | 114 |
| CTAB surface area | $m^2/g$ | 175 | 40 | 77.1 | 106 | 81 | 132 | 110 |
| DBP absorption | g/100 g | 270 | 120 | 55.5 | 185 | 156 | 203 | 193 |
| Tapped density | g/l | 90 | 430 | 79.1 | 334 | 392 | 385 | 175 |
| Alpine sieve residue 63 $\mu$m | % | n.d. | n.d. |  | 93 | 63 | 98 | 0.2 |
| Alpine sieve residue 180 $\mu$m | % | n.d. | n.d. |  | 29 | 0.6 |  | 0.02 |
| Alpine sieve residue 250 $\mu$m | % | n.d. | n.d. |  | 0.8 | 0.2 | 27 |  |
| Average PS | $\mu$m |  |  |  |  |  |  | 12.1 |

Example 5

A white opaque toothpaste was prepared from the ingredients listed below using a mixture of the precipitated silicas described in Example 3 (ratio A to B is 30:70).

| Substance | Weight % |
|---|---|
| Silica from Example 3 | 20.00 |
| Sorbitol, 70 & strength solution | 40.00 |
| Water | 31.69 |
| Polyethylene glycol 400 | 3.50 |
| Sodium lauryl sulfate | 1.20 |
| Carboxymethylcellulose | 1.20 |
| Sodium monofluorophosphate | 0.76 |
| Titanium dioxide | 0.40 |
| Methylparaben, sodium salt | 0.15 |
| Saccharin, sodium salt | 0.10 |
| Flavor | 1.00 |

In order to ensure effective homogenization, the paste was prepared in a mixer and then processed mechanically a number of times on a triple-roll mill.

Example 6

A transparent toothpaste was prepared from the ingredients listed below using a mixture of the precipitated silicas described in Example 3 (ratio A to B is 30:70).

| Substance | Weight % |
|---|---|
| Silica from Example 3 | 20.00 |
| Glycerol, 99% pure | 20.00 |
| Sorbitol, 70% strength solution | 40.00 |
| Water | 12.09 |
| Polyethylene glycol 400 | 3.50 |
| Sodium lauryl sulfate | 1.30 |
| Carboxymethylcellulose | 0.60 |
| Sodium monofluorophosphate | 0.76 |
| Dye FD&C No. 1, 1% strength solution | 0.50 |
| Methylparaben, sodium salt | 0.15 |
| Saccharin, sodium salt | 0.10 |
| Flavor | 1.00 |

The disclosure of German priority application 10112650.6 filed Mar. 16, 2001, is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by Letters Patent is:

1. A silica comprising at least two silica fractions, wherein the at least two silica fractions differ by at least 10% in their BET surface area values, their CTAB surface area values or their DBP absorption values, the ranges of these three physicochemical properties being as follows:

| BET surface area | 30–300 $m^2/g$ |
|---|---|
| CTAB surface area | 30–300 $m^2/g$ |
| DBP absorption | 80–300 g/100 g. |

2. The silica as claimed in claim 1, which is in the form of particles having an average diameter of more than 80 $\mu$m.

3. The silica as claimed in claim 1, wherein the proportion of one silica fraction in the mixture of silica fractions ranges from 5 to 95% by weight.

4. The silica as claimed in claim 1, wherein at lease one of the silica fractions comprises a precipitated silica.

5. The silica as claimed in claim 1, wherein the silica fractions are prepared by precipitating silicate with an acid and the resulting precipitation suspensions are mixed.

6. The silica as claimed in claim 1, wherein each of the silica fractions is prepared by precipitating a silicate with an acid and then filtering the precipitated silicate, followed by mixing resulting filtercakes.

7. The silica as claimed in claim 1, wherein each of the silica fractions is prepared by precipitating a silicate with an acid and then liquifying each filtercake of ready-dried silica, followed by mixing the resulting suspensions.

8. The silica as claimed in claim 1, wherein at least one silica fraction comprises a pyrogenic silica.

9. The silica as claimed in claim 1, wherein the silica fractions are mixed in the dry state.

10. A process for preparing silicas comprising at least two silica fractions, which comprises:

mixing at least two silica fractions with each other which differ by at least 10% in their values of BET surface area, CTAB surface area and DBP absorption, wherein their BET surface area values, their CTAB surface area values or their DBP absorption values, the ranges of these are as follows:

| | |
|---|---|
| BET surface area | 30–300 m$^2$/g |
| CTAB surface area | 30–300 m$^2$/g |
| DBP absorption | 80–300 g/100 g. |

11. The process as claimed in claim 10, wherein the silica is in the form of particles having an average diameter of more than 80 µm.

12. The process as claimed in claim 10, wherein the silica has the following physicochemical data:

| | |
|---|---|
| BET surface area | 30–300 m$^2$/g |
| CTAB surface area | 30–300 m$^2$/g |
| DBP absorption | 80–300 g/100 g. |

13. The process as claimed in claim 10, wherein the amount of one silica fraction in the silica product ranges from 5 to 95% by weight.

14. The process as claimed in claim 10, wherein one or more silica fractions comprise a precipitated silica.

15. The process as claimed in claim 10, wherein the silica fractions are prepared by precipitating silicate with an acid and then mixing the resulting precipitation suspensions.

16. The process as claimed in claim 10, wherein each of the silica fractions is prepared by precipitating a silicate with an acid and then filtering the precipitated silicate, followed by mixing the resulting filtercakes.

17. The process as claimed in claim 10, wherein each of the silica fractions is prepared by precipitating a silicate with an acid and then liquifying the filtercake of ready-dried silica, followed by mixing the resulting suspensions.

18. The process as claimed in claim 10, wherein at least one silica fraction comprises a pyrogenic silica.

19. The process as claimed in claim 10, wherein the silica fractions are mixed in the dry state.

20. A method of preparing a dental care composition, comprising:

in the admixing of the ingredients of the composition, admixing the silica product of claim 1 therein.

21. A method of preparing an abrasive paste, comprising:

in the admixing of the ingredients of the abrasive paste, admixing the silica product of claim 1 therein.

* * * * *